(12) United States Patent
Shen

(10) Patent No.: US 10,245,382 B2
(45) Date of Patent: Apr. 2, 2019

(54) PNEUMATIC NEEDLE-FREE INJECTION DEVICE

(71) Applicant: Liang-Chi Shen, Taoyuan (TW)

(72) Inventor: Liang-Chi Shen, Taoyuan (TW)

( * ) Notice: Subject to any disclaimer, the term of this patent is extended or adjusted under 35 U.S.C. 154(b) by 182 days.

(21) Appl. No.: 15/252,558

(22) Filed: Aug. 31, 2016

(65) Prior Publication Data

US 2018/0056002 A1    Mar. 1, 2018

(51) Int. Cl.
*A61M 5/30* (2006.01)

(52) U.S. Cl.
CPC ....... *A61M 5/30* (2013.01); *A61M 2205/3317* (2013.01); *A61M 2205/50* (2013.01); *A61M 2205/8218* (2013.01); *A61M 2205/8225* (2013.01)

(58) Field of Classification Search
CPC .... A61M 2005/006; A61M 2005/3123; A61M 5/19; A61M 5/30; A61M 5/484; A61M 2205/8218; A61M 2205/8225
See application file for complete search history.

(56) References Cited

U.S. PATENT DOCUMENTS

2004/0035491 A1 *  2/2004  Castellano ............. A61M 5/30
                                                          141/27

* cited by examiner

*Primary Examiner* — Shefali D Patel
(74) *Attorney, Agent, or Firm* — Rosenberg, Klein & Lee

(57) ABSTRACT

A pneumatic needle-free injection device restores pressured air in a pressure room to deliver high pressure air instantaneously, so as to inject a dose subcutaneously, intradermally, and intramuscularly, accelerating an absorption process of skins. The device can be further linked to a high-pressured air container for portable usage.

7 Claims, 14 Drawing Sheets

PNEUMATIC NEEDLE-FREE INJECTION DEVICE

BACKGROUND OF THE INVENTION

1. Field of the Invention

The present invention relates to a needle-free injection device, particularly to one that operates pneumatically by instantaneous high pressure deliverance.

2. Description of the Related Art

Most people are afraid of injections because of the needle. Needle-free injections are therefore developed to deliver a dose with a fine stream of fluids so that the liquid would be absorbed efficiently without incurring any wounds on the skins.

Currently needle-free injections are operated by pressured air and springs. The pressured air oriented needle-free injection technology was firstly engineered by Massachusetts Institute of Technology (MIT). It delivers doses into skins to various depths by a high-pressure jet device. Such device has an air supply device connected by a delivery tube with at least 100 cm to send in pressured air to displace a piston. However, pressured air would encounter pressure loss in the delivery process; when reaching the injection device, the pressure is not high enough for dose deliverance, resulting in the ineffectiveness of the injections and absorption of the skins. On the other hand, such injection device is not suitable for portable usage.

To overcome the problem described above, a spring operated needleless injector was disclosed in U.S. Pat. No. 8,529,500 as illustrated in FIGS. 1A and 1B. The needleless injector 10A includes an outer housing 28a, an inner housing 12a with a syringe 18a to deliver a dose of fluid to a nozzle 40a, a hammer 44a disposed in the inner housing 12a, a skin tensioning spring 30a disposed between the inner housing 12a and the outer housing 28a to push the former from the latter, and a trigger 45a linking with an injection delivery spring 36a to release the hammer 44a when the inner housing in a firing position. The device further has a skin tensioner 42a to abut on human skins at a front thereof before firing the trigger 45a to deliver a dose.

Nevertheless, there are still shortcomings of the needleless injector 10A. First of all, the device can only replace appropriate skin tensioning spring 30a and injection delivery spring 36a in accordance with skins of different organism instead of adjusting the pressure for delivery. Consequently, choices of the liquids are restricted within a range based on the choice of the skin tensioning spring 30a and the injection delivery spring 36a. In addition, since the device is operated by springs, it cannot perform continuous multi-doses. Also, there are safety issues if the trigger 45a is inadvertently pulled. Such device can also be seen in U.S. Pat. No. 7,618,393 and U.S. Pat. No. 9,333,300.

FIG. 1C illustrates another needleless injector 10B disclosed in U.S. Pat. No. 9,067,019. The device has similar structure as the needleless injector 10A described above; the differences lies in that the device 10B has a handle 11b and a trigger 12b like a handgun, and that a syringe 13b is disposed above a barrel 14b for deliverance. Such device can also be seen in U.S. Pat. No. 7,357,781.

With rising of aesthetic medicine, such devices with needle-free injection function are back into business. Furthermore, it is desirable to overcome the defects disclosed and further improve the problems for such devices.

SUMMARY OF THE INVENTION

A primary object of the present invention is to provide a pneumatic needle-free injection device that restores pressured air in a pressure room to deliver high pressure air instantaneously in order to inject the dose subcutaneously, intradermally and intramuscularly, and therefore accelerate the absorption process of skins.

Another object of the present invention is to provide a pneumatic needle-free injection device that can be further connects to a high-pressured air container for portable usage.

In order to achieve the objects above, the present invention comprises following components:

a hollow tube body including a first connecting end, a second connecting end, and at least one through hole;

a linking element including a first linking end to be engaged with the second connecting end of the tube body, a first concave formed at said first linking end, a second linking end, and a second concave formed at said second linking end; said first concave and second concave having a linking through hole in-between;

a rear section including a third connecting end to be engaged with the second linking end of the linking element, a first axial hole linking to the second concave of the linking element, and a screw hole at the opposite end of the third connecting end;

a solenoid disposed inside the tube body, including a coil, a hollow tube inside the coil, and an electric wire connected to the coil and passing through the through hole of the tube body;

a PCB disposed outside the tube body and electrically connected to the electric wire to control operation of the coil;

an engaging element fixedly engaging a rear section of the hollow tube with one end and the first concave with the other end, and having a second axial hole therein which links to the linking through hole;

a movable element being disposed inside the hollow tube at a front section thereof and having a third axial hole therein, said movable element being displaceable by a magnetic force from the solenoid;

a storage device including a cylinder and a cap; said cylinder having a front end thereof as a shrunk opening and said cap covering a rear opening of the cylinder to be engaged within the first connecting end of the tube body; said cap further having a through hole to be engaged with a front section of the hollow tube;

a moving rod having a tail end to be connected to the movable element and a front end with an abutting section which has a greater diameter than the shrunk opening to be displaced for controlling opening and closing of the shrunk opening, said abutting section having a stick extending from a front thereof and stretching into the shrunk opening, and said tail end having a fourth axial hole linking to the third axial hole, a front of the fourth axial hole further having at least one radial hole;

a first spring disposed in the second axial hole of the engaging element and the third axial hole of the movable element to provide elasticity for the movable element and the moving rod and displace the abutting section forward to close the shrunk opening and define a pressure room inside the storage device, sending pressured air to the first, second, third, and fourth axial holes in sequence and then to the pressure room via the at least one radial hole;

a housing for disposing all of said components and leaving a front end of the shrunk opening exposed, said housing further having at least one button on a surface thereof electrically connected to the PCB; and a pressure delivery tube engaged the front end of the shrunk opening with a delivery hole therein connecting the shrunk opening;

whereby the solenoid holds control of displacement of the movable element and the abutting section to ensure circulation of the shrunk opening for pressured air in the pressure room to be delivered in high speed and under high pressure into the delivery hole via the shrunk opening.

Furthermore, the device has the following structures. A space is formed between the first axial hole and the second concave. A piston is disposed in said space, including a plug end abutting an inner wall of the space, a hollow stick engaged with the plug end and extended into the first axial hole, and a fifth axial hole formed within the hollow stick and the plug end. A second spring engages through the hollow stick and has one end thereof abutting on a bottom of the space and the other end thereof abutting on a rear of the plug end to provide axial pushing force for the piston in operation.

In addition, an adjusting bolt engages the screw hole of the first axial hole for displacement and has a front end thereof abutting an end of the hollow stick. A pressurizing device is arranged at a lower place of the rear section and engaged a second connecting element, including a first passage connecting the first axial hole with an end thereof and a second passage with the other end thereof, and a third passage connecting the second passage with an end thereof and a pressurizing space formed around the pressurizing device with the other end thereof. A pressure controller engages the pressurizing device by a rotatable element, allowing the pressure controller to rotate at a pre-determined angle, said pressure controller further including an inlet, a nozzle, and an outlet, said inlet engaging a bottle end of a high-pressured air container and abutting the nozzle; a curved section blocking the pressurizing space when said pressure controller remaining unrotated and when the pressure controller being rotated at a pre-determined angle, the outlet connecting the pressurizing space of the third passage for the high-pressured air in the high-pressured air container passing through the nozzle and the outlet to flow into the pressurizing space, then delivered to the first axial hole via the third, second, and first passage sequentially; and a stopper detachably engages the second connecting element.

With features disclosed above, the present invention overcomes the problem of pressure loss during deliverance by restoring pressured air in the pressure room to deliver instantaneous high pressure dose for absorption of the skin without physical hurts. Moreover, the present invention is able to connected to a high-pressured air container for conveniently portable usage.

DETAILED DESCRIPTION OF THE PREFERRED EMBODIMENT

Figure 1A:
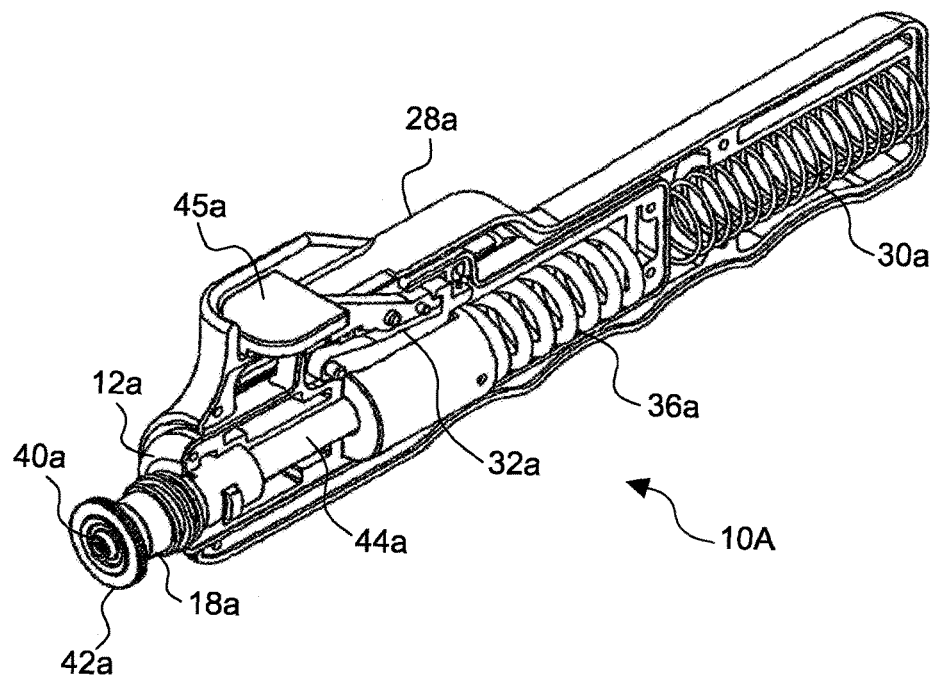
FIG. 1A is a schematic diagram of structure of a needle-free injection device disclosed in U.S. Pat. No. 8,529,500.
Figure 1B:
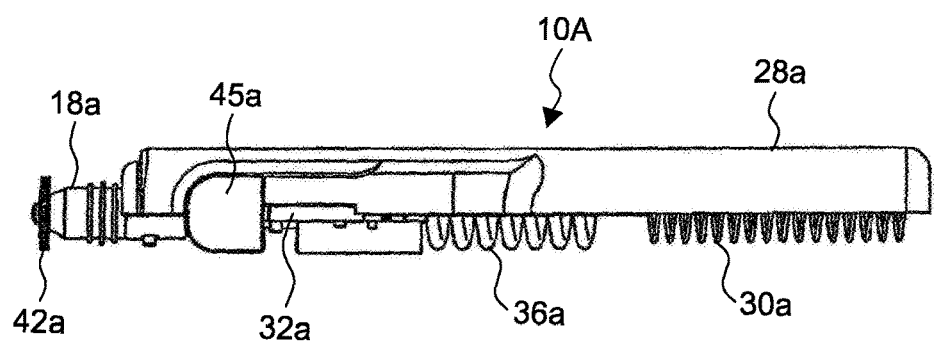
FIG. 1B is a right side elevation view of FIG. 1A.
Figure 1C:
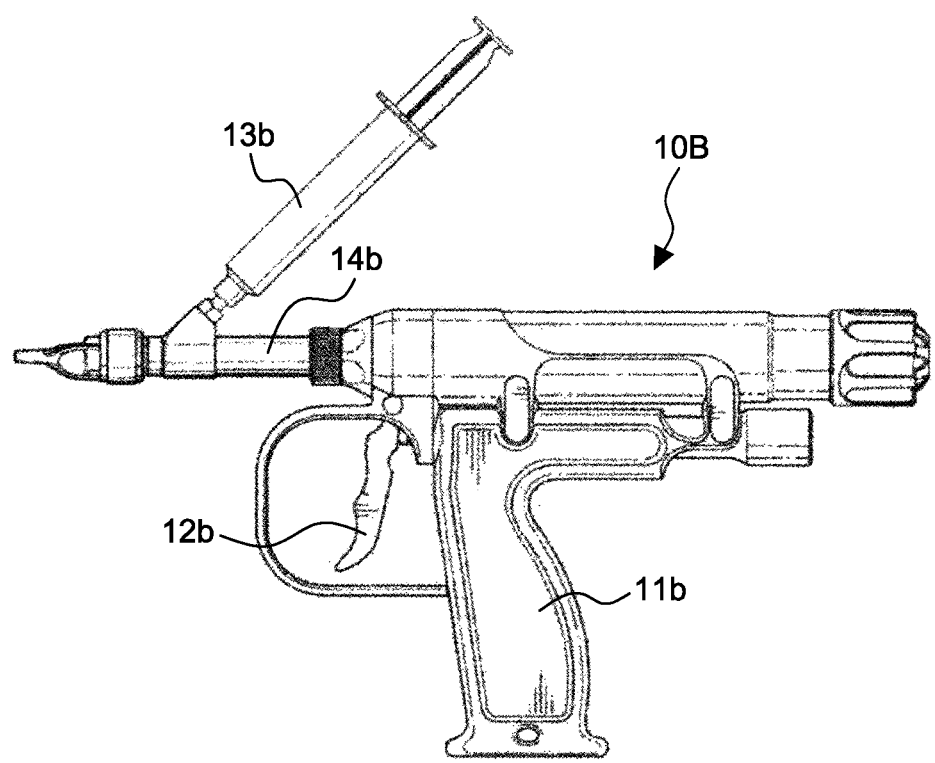
FIG. 1C is a perspective view of a needle-free injection device disclosed in U.S. Pat. No. 9,067,019.

Referring to FIGS. 2-7, in a preferred embodiment the present invention mainly comprises a tube body 10, a linking element 20, a rear section 30, a solenoid 40, a PCB 44, an engaging element 50A, a movable element 50B, a storage device 70, a moving rod 60, a first spring 52, a housing 200, and a pressure delivery tube 80.

Figure 7A:
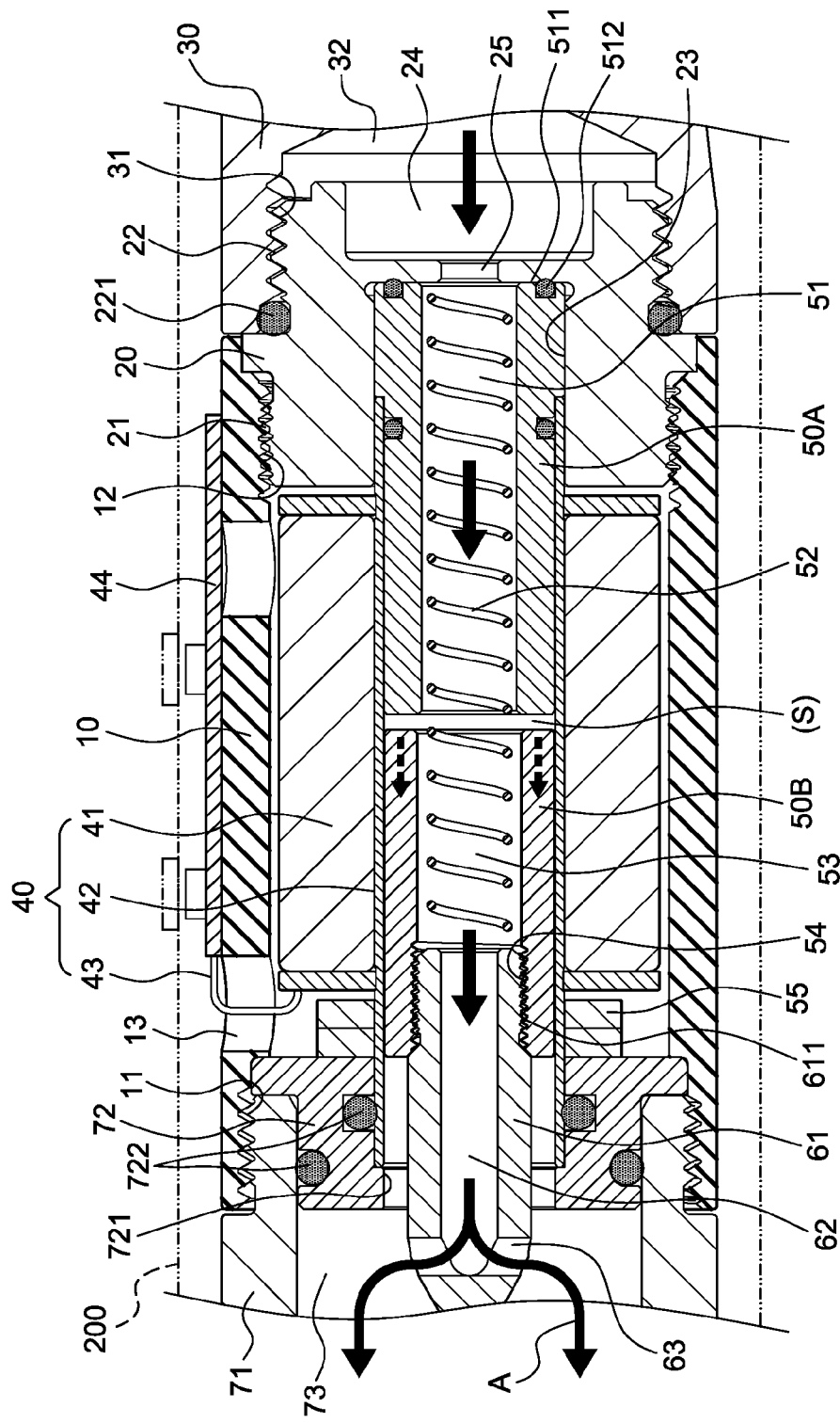
FIG. 7A is an enlarged view of area 7A in FIG. 5.
Figure 7B:
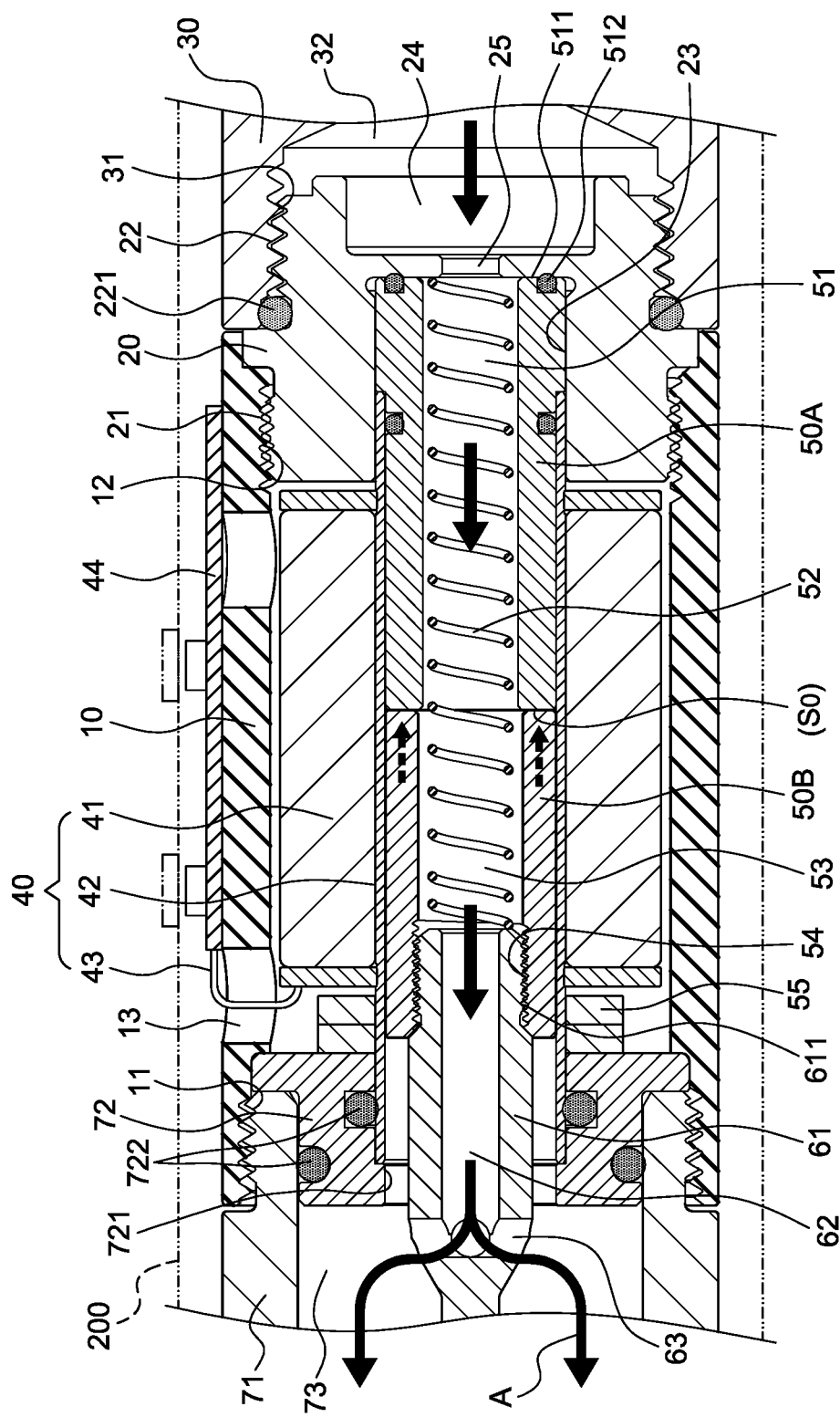
FIG. 7B is an enlarged view of area 7B in FIG. 6.
Figure 7D:
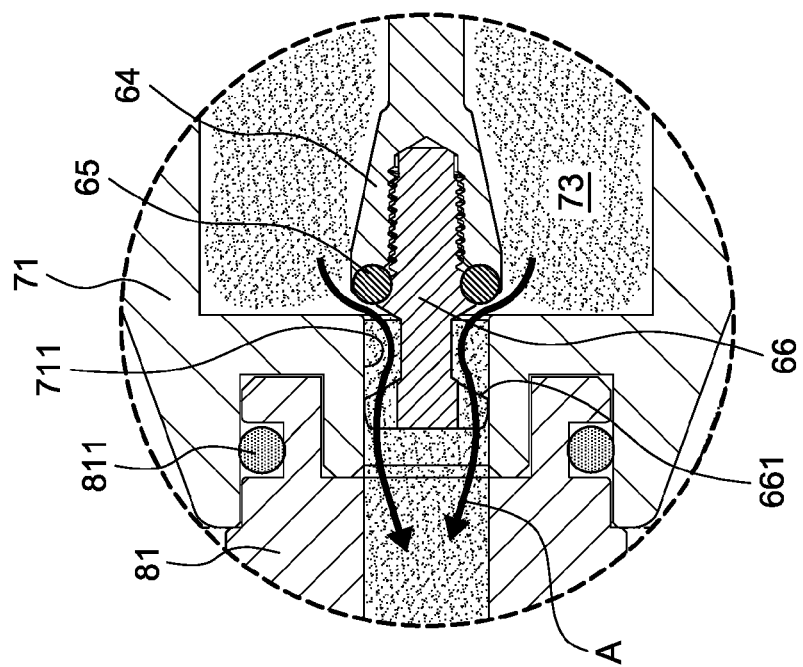
FIG. 7D is an enlarged view of area 7D in FIG. 6.

The hollow tube body 10 includes a first connecting end 11, a second connecting end 12, and at least one through hole 13. In this embodiment, the first and second connecting ends 11, 12 are threaded sections for engagement as shown in FIG. 7A.

The linking element 20 includes a first linking end 21 to be engaged with the second connecting end 12 of the tube body 10, a first concave 23 formed at the first linking end 21, a second linking end 22, and a second concave 24 formed at the second linking end 22. The first concave 23 and second concave 24 have a linking through hole 25 arranged in-between. In this embodiment, the first and second linking ends 21, 22 are threaded sections for engagement, and the second linking end 22 has a first O-ring 221 arranged around an outer periphery thereof.

Figure 3:
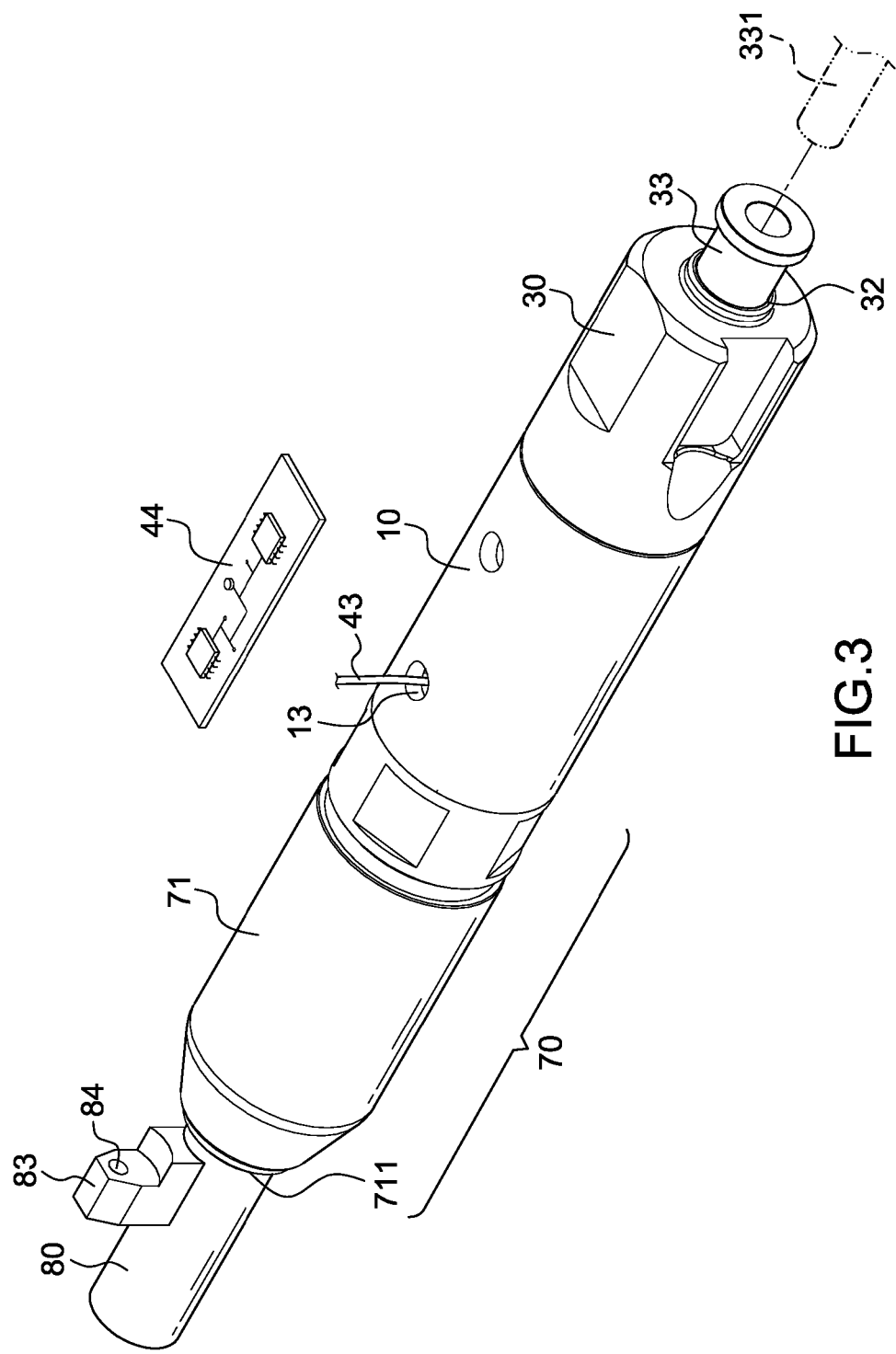
FIG. 3 is a perspective view of FIG. 2.
Figure 4:
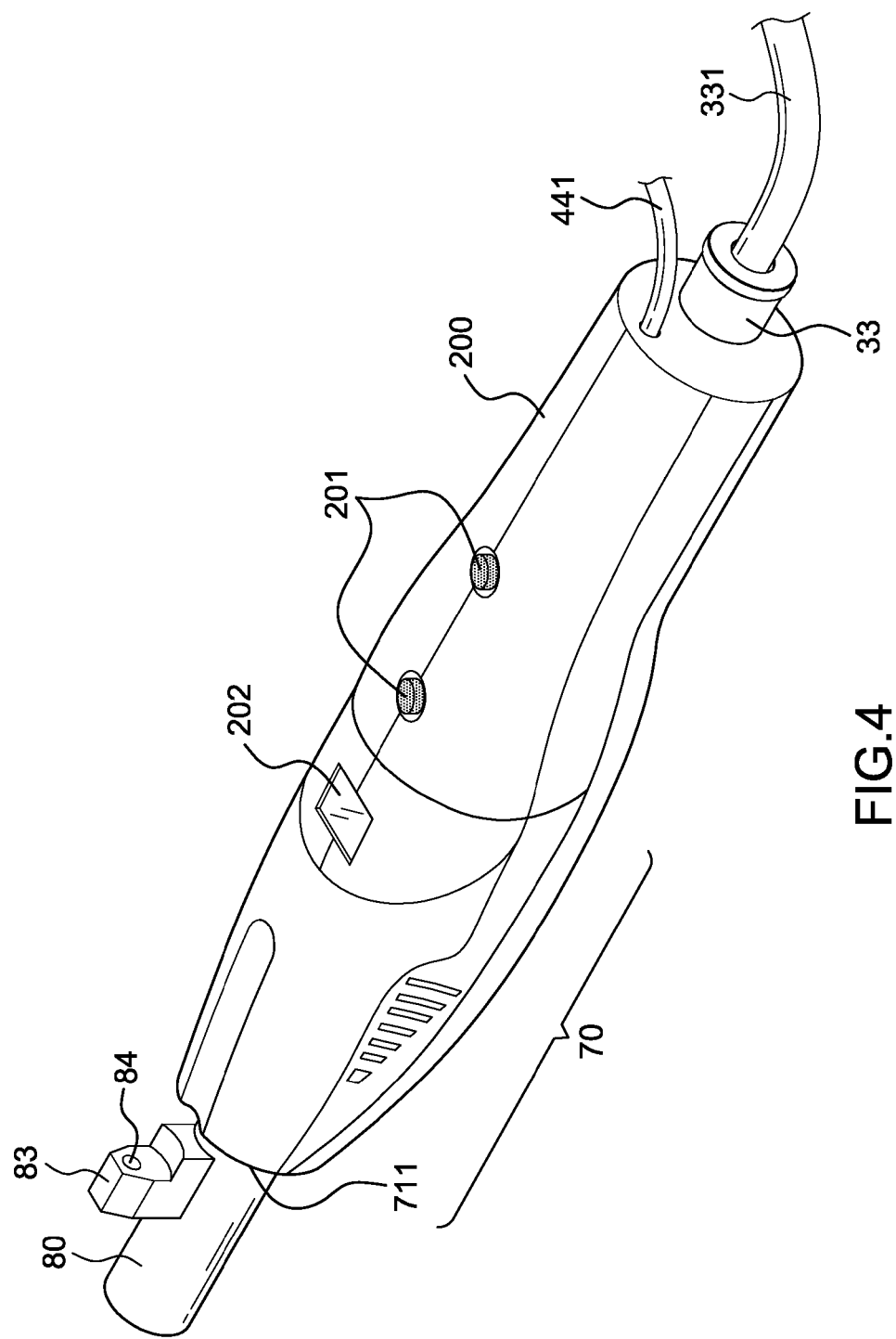
FIG. 4 is a perspective view of the present invention covered by a housing.

The rear section 30 includes a third connecting end 31 to be engaged with the second linking end 22 of the linking element 20, a first axial hole 32 linking to the second concave 24 of the linking element 20, and a screw hole 321 at the opposite end of the third connecting end 31. The screw hole 321 further connects a first connecting element 33 to link up with an air supply tube 331 as shown in FIGS. 3 and 4. In this embodiment, the third connecting end 31 is a threaded section for engagement.

The solenoid 40 is disposed inside the tube body 10, including a coil 41, a hollow tube 42 inside the coil 41, and an electric wire 43 connected to the coil 41 and passing through the through hole 13 of the tube body 10. The PCB 44 is disposed outside the tube body 10 and electrically connected to the electric wire 43 to control operation of the coil 41.

The engaging element 50A is fixedly engaging a rear section of the hollow tube 42 with one end and the first concave 23 with the other end, and is has a second axial hole 51 therein linking to the linking through hole 25. In this embodiment, a second O-ring 512 is arranged around a rear end 511 of the engaging element 50A, abutting on a bottom of the first concave 23 for sealing as shown in FIG. 7A. The movable element 50B is disposed inside the hollow tube 42 at a front section thereof and has a third axial hole 53 therein. During operation, it is displaceable by a magnetic force from the solenoid 40.

The storage device 70 includes a cylinder 71 and a cap 72. The cylinder 71 has a front end thereof as a shrunk opening 711 and the cap 72 is covering a rear opening 712 of the cylinder 71 to be engaged within the first connecting end 11 of the tube body 10. The cap 72 further has a through hole 721 to be engaged with a front section of the hollow tube 42. In this embodiment, the cap 72 has two third O-rings 722, one of which is arranged around an inner periphery thereof to seal with the hollow tube 42 and the other one is arranged around an outer periphery thereof to seal with the cylinder 71 as shown in FIG. 7A. The hollow tube 42 further has at least one gasket 55 at a front end thereof.

Figure 2:
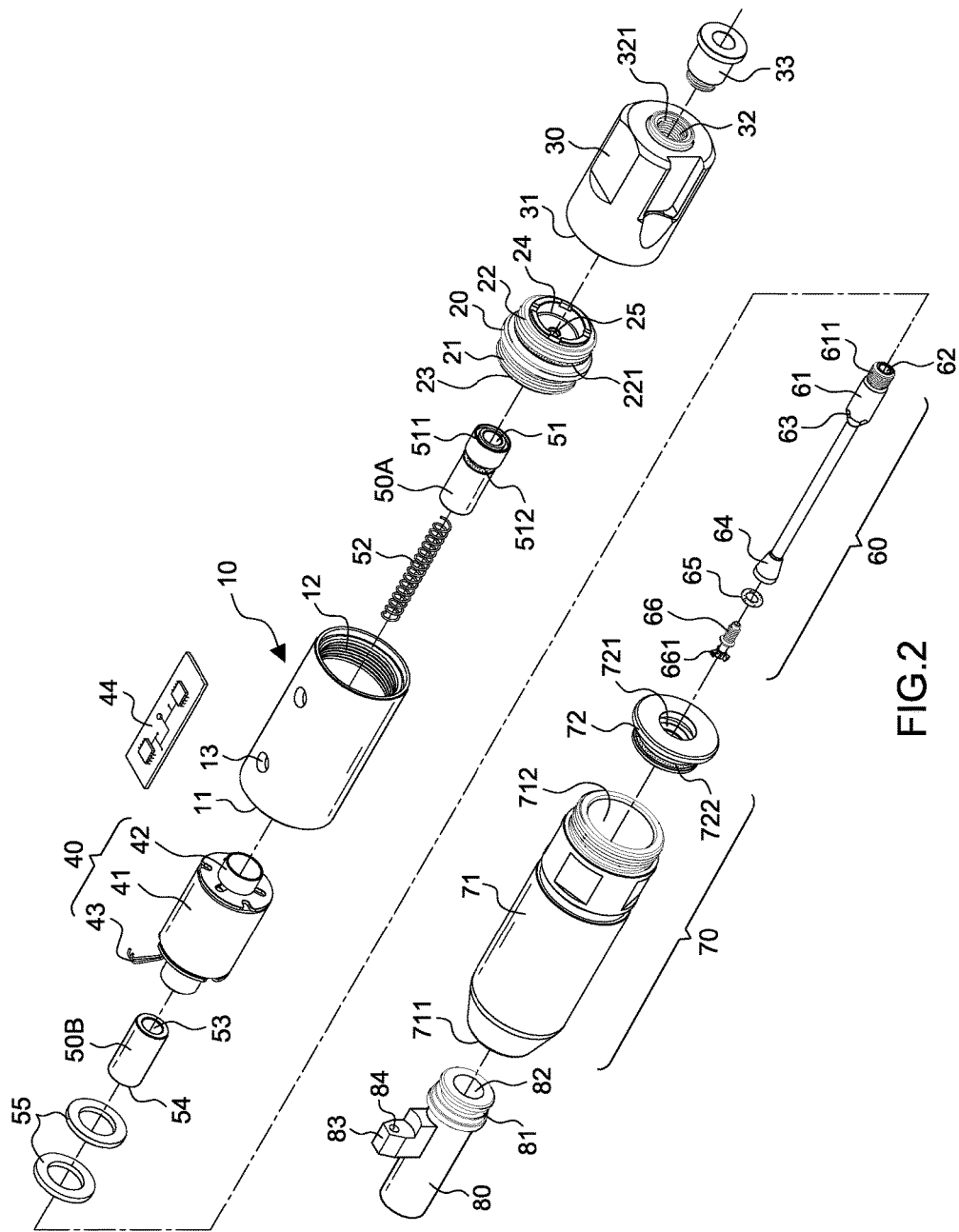
FIG. 2 is an exploded view of the present invention in a first embodiment.
Figure 7C:
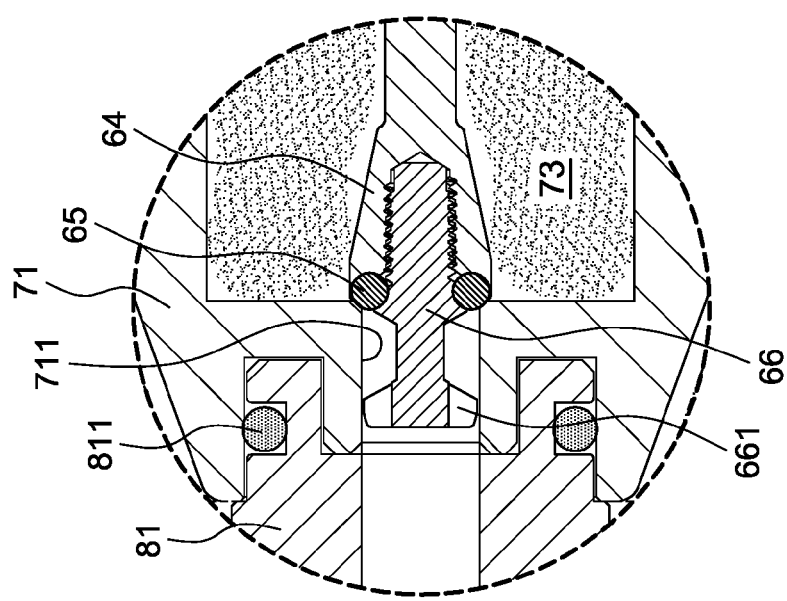
FIG. 7C is an enlarged view of area 7C in FIG. 5.

The moving rod 60 has a tail end 61 to be connected to the movable element 50B and a front end with an abutting section 64 which has a greater diameter than the shrunk opening 711 to be displaced for control of opening and closing of the shrunk opening 711. The tail end 61 and the movable element 50B are engaged by screwing and tail end 61 has a fourth axial hole 62 linking to the third axial hole 53; a front of the fourth axial hole 62 further has at least one radial hole 63 as shown in FIGS. 2 and 7C. The abutting section 64 further has a fourth O-ring 65 arranged at a front end thereof and a stick 66 extending from the front and stretching into the shrunk opening 711. In this embodiment, the stick 66 has a plurality of axial blades 661 arranged at a front section thereof to enhance the stability during displacement without blocking pressured air A passing through the shrunk opening 711.

The first spring 52 is disposed in the second axial hole 51 of the engaging element 50A and the third axial hole 53 of the movable element 50B to provide elasticity for the movable element 50B and the moving rod 60, thus displacing the abutting section 64 forward to close the shrunk opening 711 and define a pressure room 73 inside the storage device 70, sending pressured air A to the first, second, third, and fourth axial holes 32, 51, 53, 62 in sequence and then to the pressure room 73 via the at least one radial hole 63.

The housing 200 is for disposing all of said components and leaving a front end of the shrunk opening 711 exposed as shown in FIG. 4. The housing 200 further has at least one button 201 on a surface thereof electrically connected to the PCB 44, and it may have a screen 202 thereon if needed. Also, the design of the housing 200 is adaptable for conveniently holding and operating. In this embodiment, the housing 200 is connected to an external wire 441 for power supply for the PCB 44. The housing can also have batteries (not shown) for power supply as well.

The pressure delivery tube 80 has a rear end 81 thereof engaging the front end of the shrunk opening 711 with a delivery hole 82 therein connecting the shrunk opening 711. In this embodiment, the pressure delivery tube 80 further includes a delivery source connector 83 which has an insertion passage 84 for connection to a replaceable tube or container 85 for deliverance.

Figure 5:
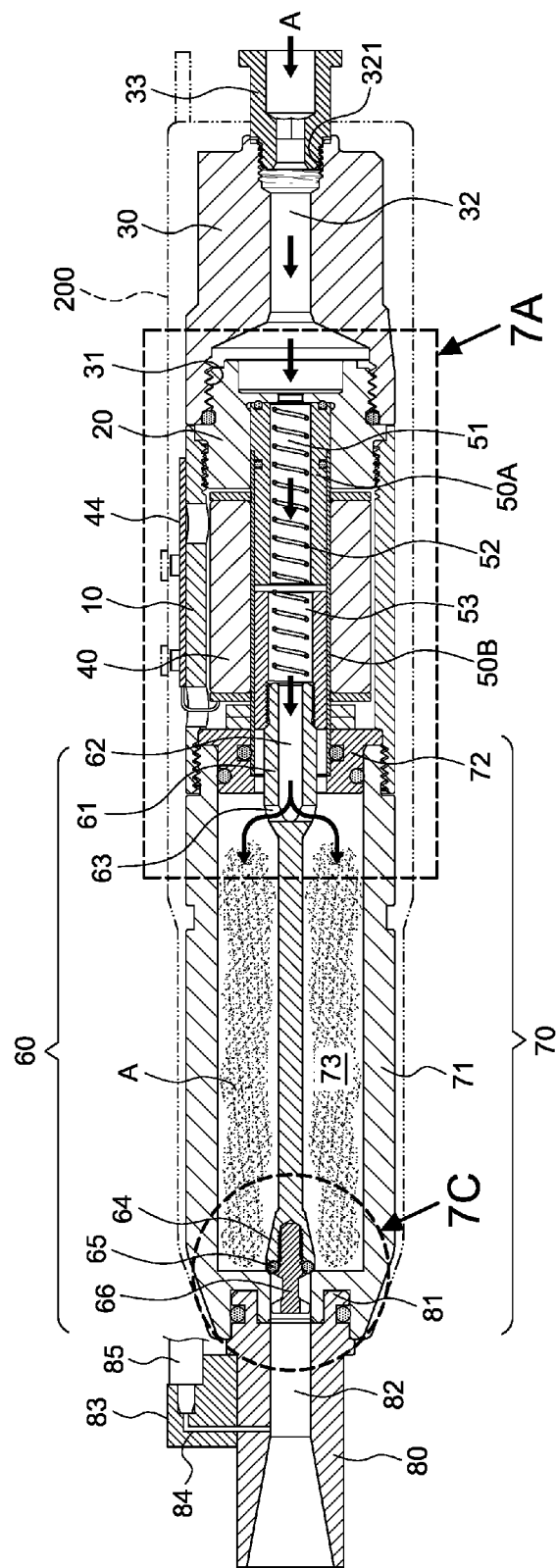
FIG. 5 is a sectional view of the present invention illustrating a movable element and a moving rod displacing forward to close a shrunk opening.
Figure 6:
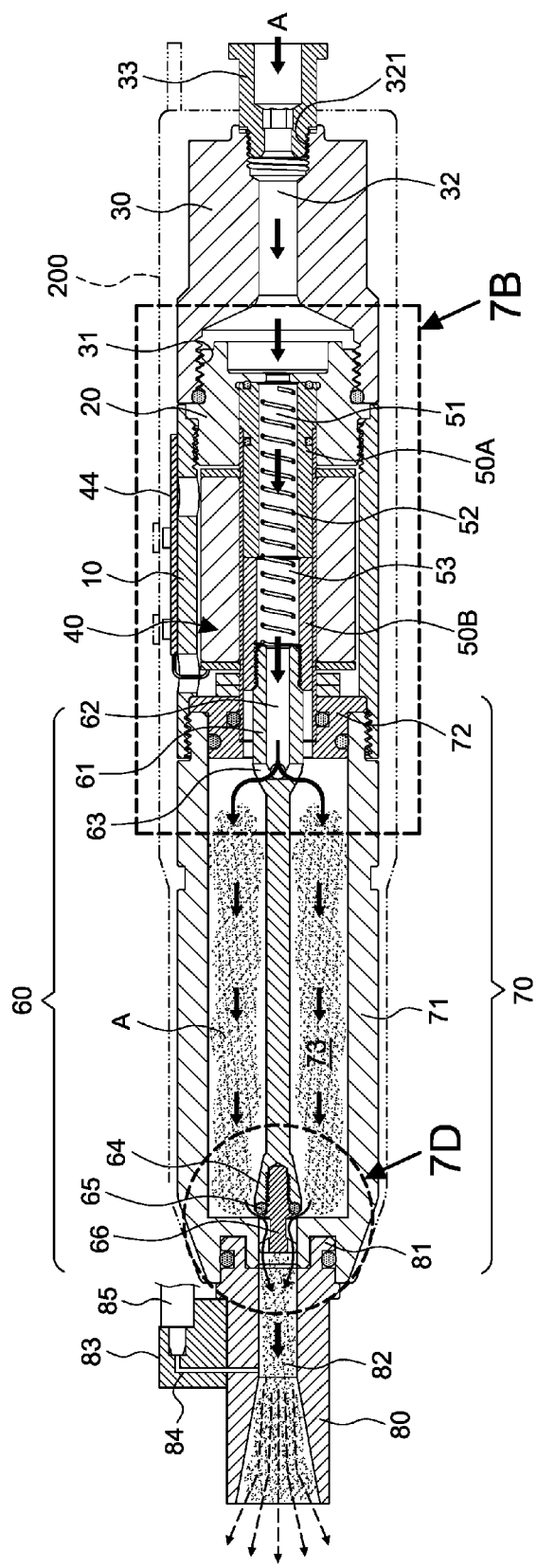
FIG. 6 is a sectional view of the present invention illustrating the movable element and the moving rod displacing backward to open the shrunk opening.

Further referring to FIGS. 5, 7A and 7C, when electricity through the coil 41 of the solenoid 40 is interrupted, the first spring 52 would produce a elasticity for the movable element 50B and the moving rod 60 to displace forward, forming a gap S between the movable element 50B and the engaging element 50A and forcing the abutting section 64 displacing forward to close the shrunk opening 711. Therefore, pressured air A is able to flow through the first, second, third, and fourth axial holes 32, 51, 53, 62 in sequence and then to the pressure room 73 via the at least one radial hole 63 to be restored in the pressured room 73. Then referring to FIGS. 6, 7B, and 7D, when the coil 41 of the solenoid 40 is electrified, a magnetic force is produces to displace the movable element 50B and the moving rod 60 backwards to abut on the engaging element 50A, eliminating the gap S and leave the shrunk opening 711 opened.

Whereby the solenoid 40 holds control of displacement of the movable element 50B and the abutting section 64 to ensure circulation of the shrunk opening 711 for pressured air A in the pressure room 73 to be delivered in high speed and under high pressure into the delivery hole 82 via the shrunk opening 711, so as to deliver a dose via the pressure delivery tube 80 efficiently and accelerate the absorption process of the skin.

FIGS. 8-11 disclosed structures of the present invention in another embodiment. The differences and features in this embodiment lie in that a space 34 is formed between the first axial hole 32 and the second concave 24; a piston 35 is disposed in the space 34, including a plug end 351 abutting an inner wall of the space 34, a hollow stick 352 engaged with the plug end 351 and extended into the first axial hole 32, and a fifth axial hole 353 formed within the hollow stick 352 and the plug end 351.

Further referring to FIGS. 8-11, a second spring 36 engages through the hollow stick 352 and has one end thereof abutting on a bottom of the space 34 and the other end thereof abutting on a rear of the plug end 351 to provide axial pushing force for the piston 35 in operation; an adjusting bolt 37 engages the screw hole 321 of the first axial hole 32 for displacement and has a front end 371 abutting an end 354 of the hollow stick 352. In this embodiment, the front end 371 is made of plastics or rubber to ensure the sealing function.

A pressurizing device 90 is arranged at a lower place of the rear section 30 and engaged a second connecting element 33a, including a first passage 91 connecting the first axial hole 32 with an end thereof and a second passage 92 with the other end thereof, and a third passage 93 connecting the second passage 92 with an end thereof and a pressurizing space 94 formed around the pressurizing device 90 with the other end thereof.

A pressure controller 100 engages the pressurizing device 90 by a rotatable element 101, allowing the pressure controller 100 to rotate at a pre-determined angle. The pressure controller 100 further includes an inlet 102, a nozzle 103, and an outlet 104. The inlet 102 engages a bottle end of a high-pressured air container 105 and abuts on the nozzle 103; a curved section 106 blocks the pressurizing space 94 when the pressure controller 100 remains unrotated; when the pressure controller 100 is rotated at a pre-determined angle, the outlet 104 connects the pressurizing space 94 of the third passage 93 for the high-pressured air A in the high-pressured air container 105 to pass through the nozzle 103 and the outlet 104 to flow into the pressurizing space 94, then to be delivered to the first axial hole 32 via the third, second, and first passage 93, 92, 91 sequentially. A stopper 332 detachably engages the second connecting element 33a.

Figure 8:
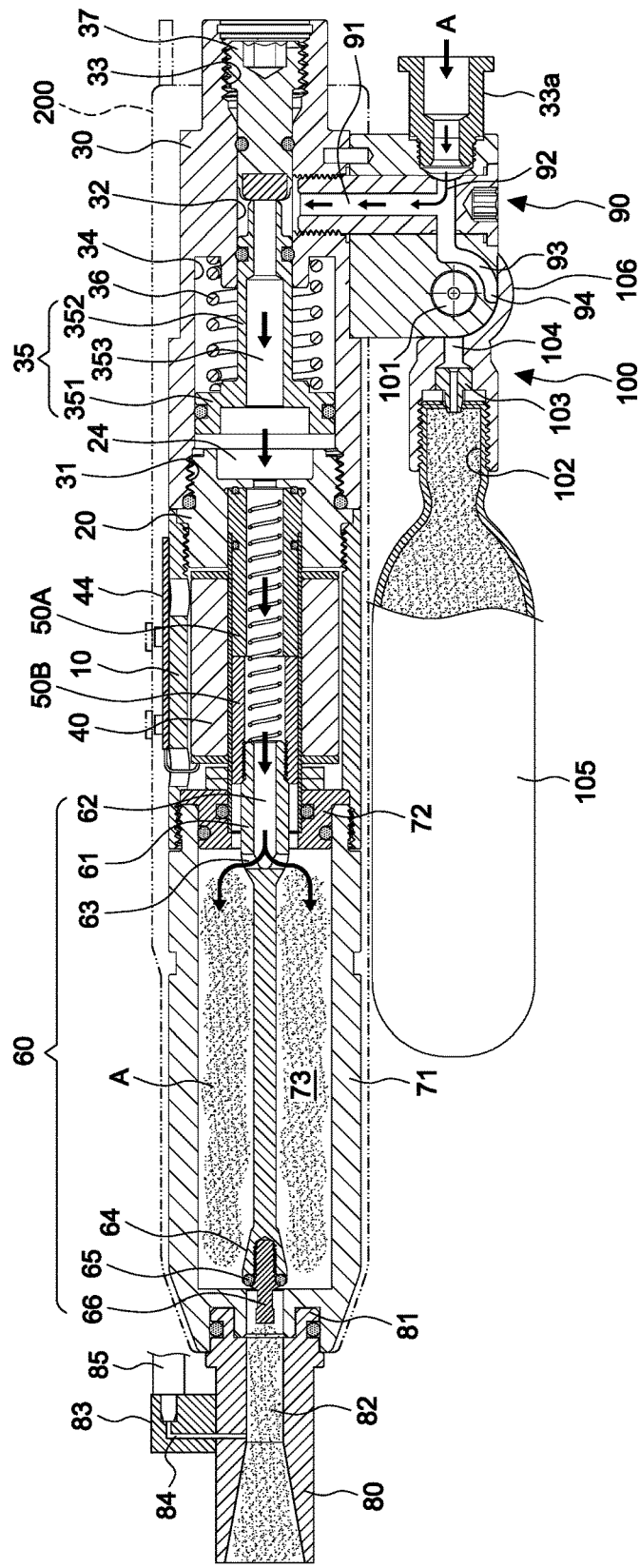
FIG. 8 is a sectional view of the present invention in a second embodiment, illustrating pressured air being supplied via a second connecting element.

In short, in this embodiment, the present invention further engages the high-pressured air container 105 so that pressured air A would be guided from the second connecting element 33a, passing through the second passage 92 and the first passage 91, then flowing into the first axial hole 32 and to the second concave 24 via the fifth axial hole 353 of the piston 35. The routine after that remains the same as in the preferred embodiment. Since pressured air A is guided from the second connecting element 33a, the present invention is able to be operated indoors by connecting to a machine for air supply with variations of the pressure set up in advance as shown in FIG. 8.

Figure 9:
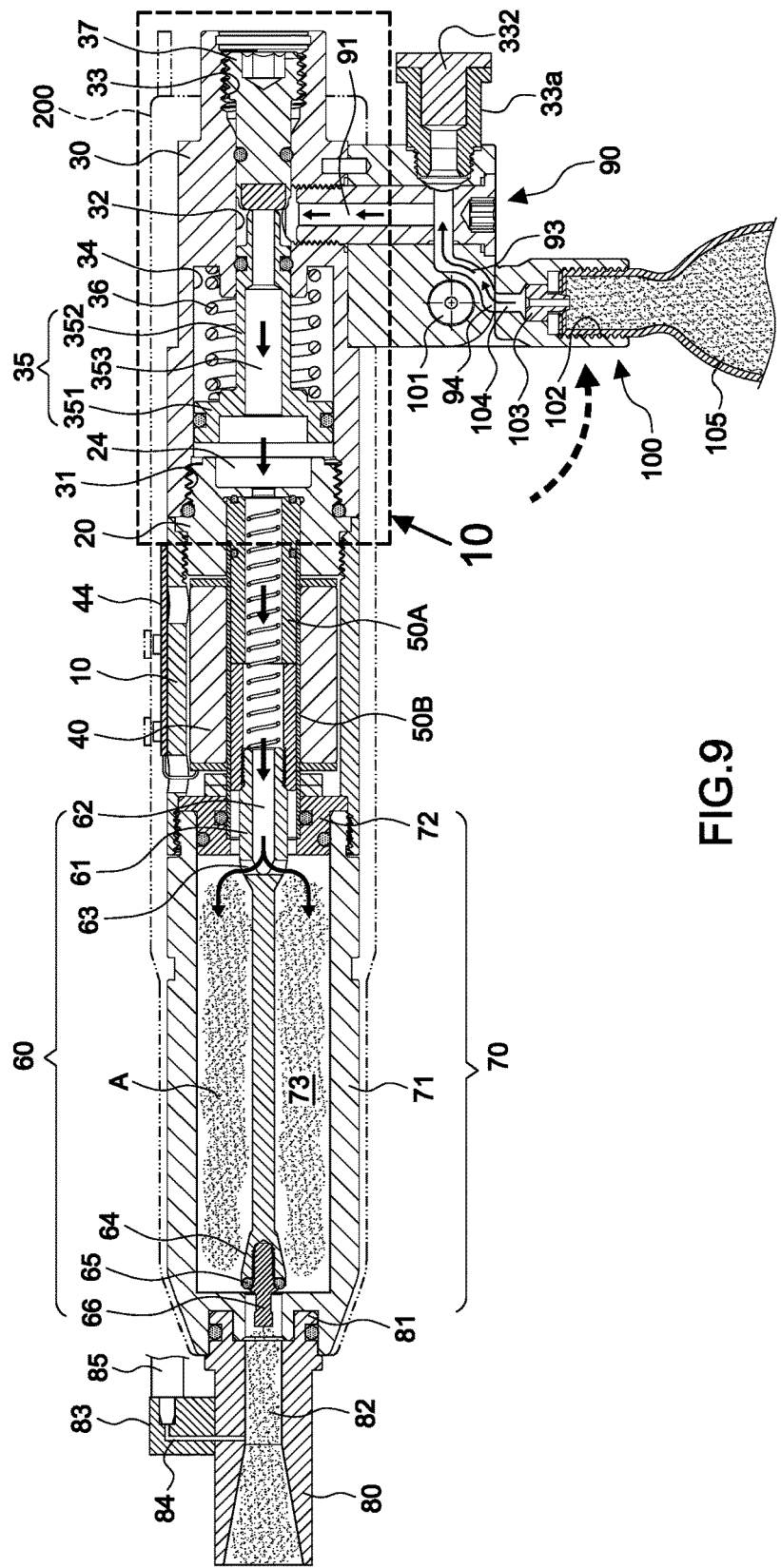
FIG. 9 is a sectional view of the present invention in the second embodiment, illustrating pressured air being supplied by a high-pressured air container.
Figure 10:
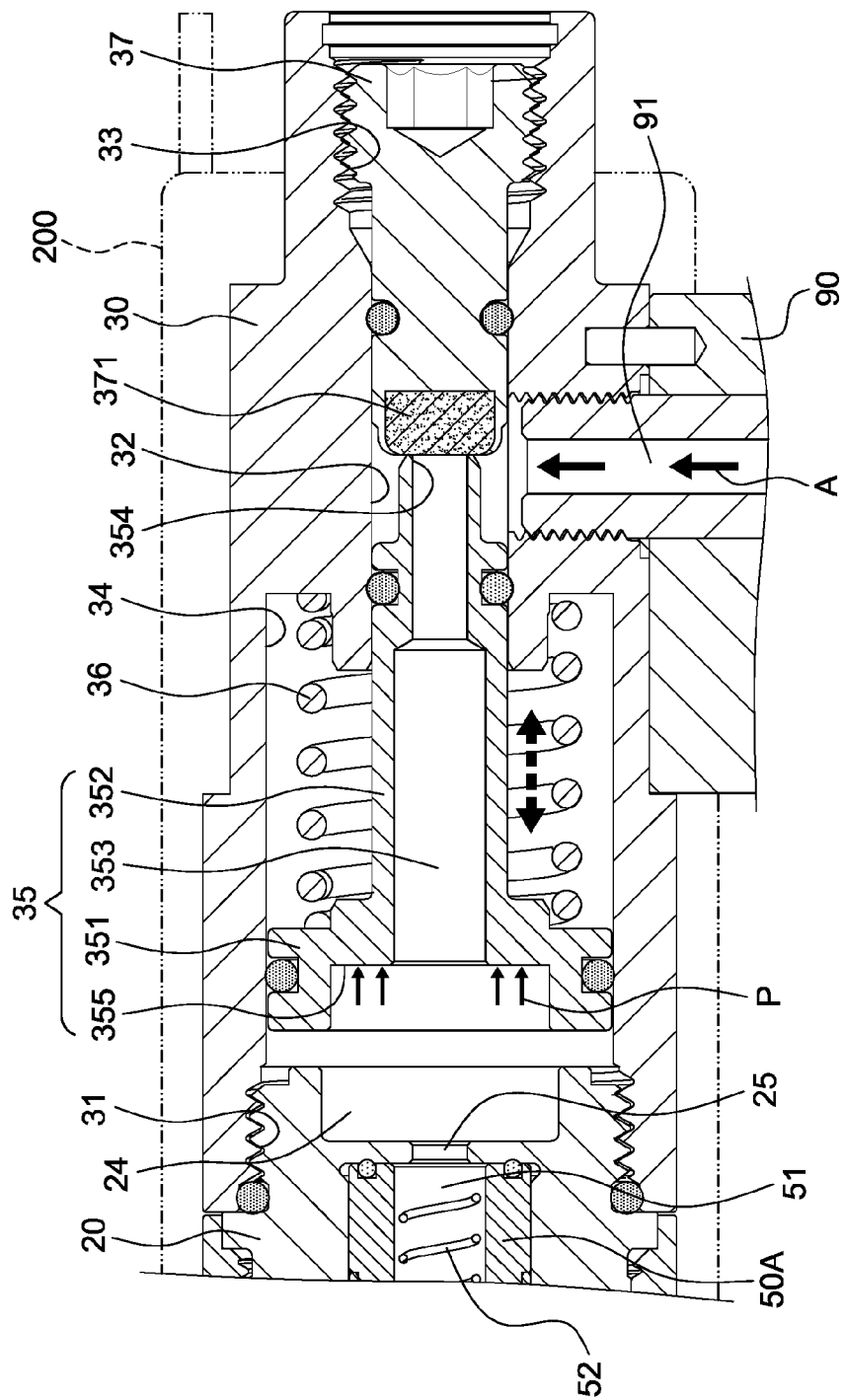
FIG. 10 is an enlarged view of area 10 in FIG. 9, illustrating a piston displacing backward.

As for outdoor usage, referring to FIG. 9, the second connecting element 33a is sealed by a stopper 332 and the pressure controller 100 is rotated by 90° to connect the outlet 104 and the pressurizing space 94, enabling the pressured air A in the high-pressured air container 105 flow into the pressurizing space 94 via the nozzle 103 and the outlet 104. The pressured air A then flows into the first axial hole 32 via the third passage 93, the second passage 92 and the first passage 91, and then reach the second concave 24 via the fifth axial hole 353 of the piston 35.

Figure 11:
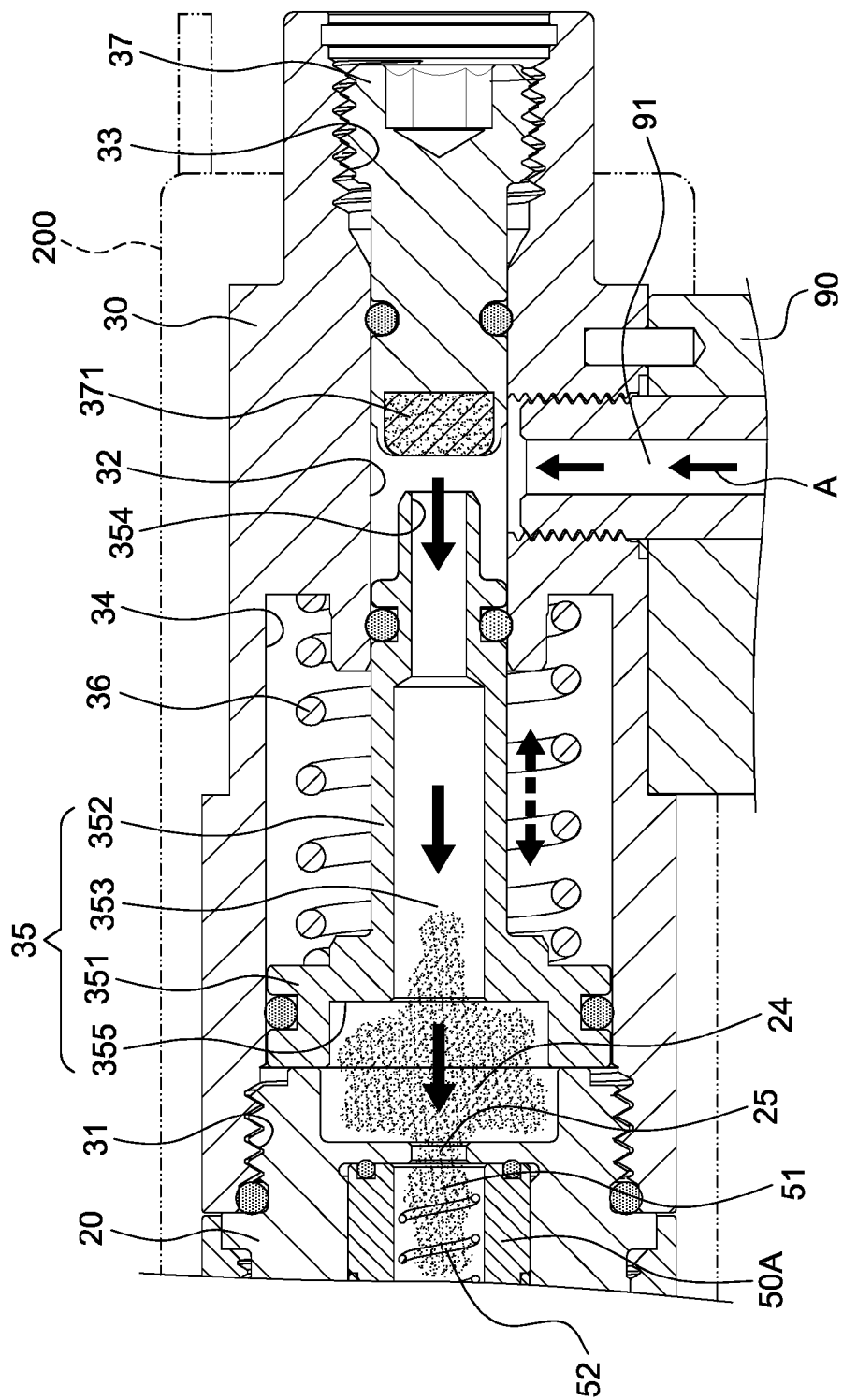
FIG. 11 is another enlarged view of area 10 in FIG. 9, illustrating a piston displacing forward.

Another difference in this embodiment is that the space 34 of the rear section 30 has the piston 35 and the second spring 36 for second pressure adjustment. That is, when the pressured air A in the high-pressured air container 105 flow through the nozzle 103 and the outlet 104, it is the first pressure adjustment and then the pressured air A flows into the first axial hole 32. Furthermore, in FIG. 11, the piston 35 is pushed by the second spring 36, and the pressured air A flows to the second concave 24 of the fifth axial hole 353 from the entry 354 of the hollow stick 352. When the pressure P of the pressured air A at a surface 355 of the plug end 351 is greater than the elasticity of the second spring 36, the piston 35 would displace backwards. Then referring to FIG. 10, the entry 354 of the hollow stick 352 is abutting on the front end 371 of the adjusting bolt 37 for sealing. When the pressured air A in the second concave 24 flows to the second axial hole 51 via the linking through hole 25 to reduce the pressure P for which to be less than the elasticity of the second spring 36, the device returns back to the status as shown in FIG. 11. The pressure difference caused to displace the piston 35 is the second adjustment for the pressured air A, and the piston 35 is controlled by the displacement of the adjusting bolt 37 along the screw hole 321. Therefore, the pressure P of the air from the high-pressured air container 105 is adjusted to be preferred for operation. The present invention thus can be applied to portable usage.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A pneumatic needle-free injection device comprising:
   a tube body having a hollow configuration and including a first connecting end, a second connecting end, and at least one through hole;
   a linking element including a first linking end engaged with the second connecting end of the tube body, a first concave portion formed at said first linking end, a second linking end, and a second concave portion formed at said second linking end; a through hole formed between said first and second concave portions;
   a rear section including a third connecting end engaged with the second linking end of the linking element, a first axial hole formed in the rear section and communicating with the second concave portion of the linking element, and a screw hole formed at an end of the rear section in opposing relationship to the third connecting end;
   a solenoid disposed inside the tube body, the solenoid including a coil, a hollow tube formed inside the coil, and an electric wire connected to the coil and passing through the at least one through hole of the tube body;
   a printed circuit board disposed outside the tube body and electrically connected to the electric wire to control operation of the coil;
   an engaging element having two ends with one end thereof fixedly engaging a rear section of the hollow tube, and another end of the engaging element fixedly engaging the first concave portion, and the engaging element having a second axial hole communicating with the through hole of the linking element;
   a movable element disposed inside the hollow tube at a front section thereof and having a third axial hole therein, said movable element being displaceable by a magnetic force from the solenoid;
   a storage device including a cylinder and a cap; said cylinder defining a shrunk opening at a front end thereof, said cap covering a rear opening of the cylinder and engaged within the first connecting end of the tube body; said cap having a through hole engaged with the front section of the hollow tube;
   a moving rod having a tail end connected to the movable element and a front end formed with an abutting section which has a greater diameter than the shrunk opening, and the moving rod being displaced for controlling opening and closing of the shrunk opening, said abutting section having a stick extending from a front thereof and the stick stretching into the shrunk opening, said tail end having a fourth axial hole communicating with the third axial hole, and a front of the tail end having at least one radial hole;
   a first spring disposed in the second axial hole of the engaging element and the third axial hole of the movable element to provide elasticity for the movable element and the moving rod and thereby displace the abutting section forward to close the shrunk opening and define a pressure room inside the storage device, wherein pressurized air flows through the first axial hole, the second axial hole, the third axial hole, and the fourth axial hole in sequence and then to the pressure room via the at least one radial hole;
   a housing having said tube body, said linking element, said rear section, said solenoid, said printed circuit board, said engaging element, said movable element, said storage device, said moving rod, and said first spring disposed therein, a front end of the shrunk opening being exposed through said housing, and said housing having at least one button on a surface thereof electrically connected to the printed circuit board; and
   a pressure delivery tube engaged to the front end of the shrunk opening with a delivery hole therein connecting to the shrunk opening;
   whereby the solenoid controls displacement of the movable element and the abutting section to ensure circulation of the pressurized air in the pressure room for delivery at high speed and under high pressure into the delivery hole via the shrunk opening.

2. The pneumatic needle-free injection device as claimed in claim 1, wherein the first connecting end, the second connecting, the first linking end and the second linking end of the linking element, the third connecting end of the rear section, and the rear opening of the cylinder are respectively formed with threaded sections.

3. The pneumatic needle-free injection device as claimed in claim 1, wherein O-rings are respectively disposed around the abutting section of the moving rod, an inner periphery of the cap, an outer periphery of the cap, the second linking end of the linking element, and a rear section of the engaging element.

4. The pneumatic needle-free injection device as claimed in claim 1, wherein the screw hole is engaged with a first connecting element.

5. The pneumatic needle-free injection device as claimed in claim 1, wherein:
- a space is formed between the first axial hole and the second concave portion;
- a piston is disposed in said space and including a plug end abutting an inner wall of the rear section within said space, a hollow stick engaged with the plug end and extending into the first axial hole, and a fifth axial hole formed within the hollow stick and the plug end;
- a second spring extends about the hollow stick and has one end thereof abutting the rear section within the space and another end thereof abutting a rear of the plug end to provide an axial pushing force for the piston in operation;
- an adjusting bolt engages the screw hole of the rear section for displacement and a front end of the adjusting bolt abuts an end of the hollow stick;
- a pressurizing device is arranged at a lower place of the rear section and engaged to a second connecting element, the pressurizing device including a first passage connecting the first axial hole with a corresponding end of the pressurizing device, a second passage connecting the first passage with a corresponding end of the pressurizing device, and a third passage connecting the second passage with a corresponding end of the pressurizing device, and a pressurizing space formed within the pressurizing device;
- a pressure controller engages the pressurizing device by a rotatable element to rotate at a pre-determined angle, said pressure controller including an inlet, a nozzle, and an outlet, said inlet engaging a bottle end of a high-pressured air container and abutting the nozzle; a curved section blocking the pressurizing space when said pressure controller remains unrotated and when the pressure controller is rotated at the pre-determined angle, the outlet connects the pressurizing space for high-pressured air in the high-pressured air container passing through the nozzle and the outlet to flow into the pressurizing space to then be delivered to the first axial hole via the third passage, the second passage, and the first passage sequentially; and
- a stopper detachably engages the second connecting element.

6. The pneumatic needle-free injection device as claimed in claim 5, wherein the first connecting end, the second connecting end, the first linking end and the second linking end of the linking element, the third connecting end of the rear section, and the rear opening of the cylinder are respectively formed with threaded sections.

7. The pneumatic needle-free injection device as claimed in claim 5, wherein O-rings are respectively disposed around the abutting section of the moving rod, an inner periphery of the cap, an outer periphery of the cap, the second linking end of the linking element, and a rear section of the engaging element.

* * * * *